US011812723B2

(12) United States Patent
Jacobs et al.

(10) Patent No.: US 11,812,723 B2
(45) Date of Patent: Nov. 14, 2023

(54) METHOD AND APPARATUS FOR BREEDING AND COLLECTING INSECT LARVAE

(71) Applicant: PreZero US, Inc., Los Angeles, CA (US)

(72) Inventors: Johan Jacobs, Turnhout (BE); Nouchka De Craene, Turnhout (BE); Stefaan Depraetere, Turnhout (BE); Zara Vermast, Turnhout (BE)

(73) Assignee: PreZero US, Inc., Los Angeles, CA (US)

( * ) Notice: Subject to any disclaimer, the term of this patent is extended or adjusted under 35 U.S.C. 154(b) by 730 days.

(21) Appl. No.: 16/966,939

(22) PCT Filed: Feb. 6, 2019

(86) PCT No.: PCT/EP2019/025040
§ 371 (c)(1),
(2) Date: Aug. 3, 2020

(87) PCT Pub. No.: WO2019/154563
PCT Pub. Date: Aug. 15, 2019

(65) Prior Publication Data
US 2021/0045368 A1 Feb. 18, 2021

(30) Foreign Application Priority Data

Feb. 7, 2018 (BE) .................................. 2018/0018

(51) Int. Cl.
*A01K 67/033* (2006.01)
*A01K 29/00* (2006.01)
(Continued)

(52) U.S. Cl.
CPC ............ *A01K 67/033* (2013.01); *A01K 29/00* (2013.01); *B65G 27/20* (2013.01); *G06V 40/10* (2022.01); *H04N 7/18* (2013.01); *H04N 23/56* (2023.01)

(58) Field of Classification Search
CPC ............ A01K 67/033; A01K 2227/706; A01K 29/00; G06V 40/10; B65G 27/20; H04N 23/56; H04N 7/18
See application file for complete search history.

(56) References Cited

FOREIGN PATENT DOCUMENTS

BE  1025664 B9  5/2019
FR  3 013 561    5/2015
(Continued)

OTHER PUBLICATIONS

International Search Report of the International Searching Authority, dated Apr. 4, 2019, from International Application No. PCT/EP2019/025040, filed on Feb. 6, 2019. 3 pages.
(Continued)

*Primary Examiner* — Yvonne R Abbott-Lewis
(74) *Attorney, Agent, or Firm* — K&L Gates LLP; Louis C. Cullman; Dennis A. Majewski

(57) ABSTRACT

The invention relates to a method for the breeding and collection of neonate larvae, in particular of the black soldier fly, containing the placing of insects in a cage, provided with means for depositing eggs, guiding larvae, hatched from the deposited eggs, by means of a guiding device, placed under the cage, under the influence of gravity to a conveyor belt placed under the guiding means, moving the larvae by means of the conveyor belt to a recipient placed at the end of the conveyor belt, counting the number of larvae on the conveyor belt before collection in the recipient, and collecting the larvae of the conveyor belt in the recipient until a predetermined number of larvae has been reached.

16 Claims, 6 Drawing Sheets

(51) Int. Cl.
  *B65G 27/20* (2006.01)
  *G06V 40/10* (2022.01)
  *H04N 7/18* (2006.01)
  *H04N 23/56* (2023.01)

(56) References Cited

FOREIGN PATENT DOCUMENTS

FR 3122551 A1 * 11/2022
WO WO 2005/102368 A1 11/2005

OTHER PUBLICATIONS

Written Opinion of the International Searching Authority, dated Apr. 4, 2019, from International Application No. PCT/EP2019/025040, filed on Feb. 6, 2019. 5 pages.
International Preliminary Report on Patentability, dated Aug. 11, 2020, from International Application No. PCT/EP2019/025040, filed on Feb. 6, 2019. 6 pages.

* cited by examiner

METHOD AND APPARATUS FOR BREEDING AND COLLECTING INSECT LARVAE

RELATED APPLICATIONS

This application is a § 371 National Phase Application of International Application No. PCT/EP2019/025040, filed on Feb. 6, 2019, now International Publication No. WO 2019/154563 A1, published on Aug. 15, 2019, which International Application claims priority to Belgian Application 2018/0018 filed on Feb. 7, 2018, both of which are incorporated herein by reference in their entirety.

FIELD OF THE INVENTION

The present invention relates to a method and an apparatus for breeding and collecting insect larvae. To this end, the method comprises introducing fertilized eggs, hatching them and collecting a specific number of insect larvae, preferably neonate larvae, in a recipient. More in particular, the invention relates to a method and apparatus for breeding (neonate) larvae of the black soldier fly.

BACKGROUND OF THE INVENTION

From the earlier Belgian patent application filed by the applicant with filing number BE 2017/0150, filing date 26 Oct. 2017, it is known that the black soldier fly, in particular larvae thereof, are extremely suitable for processing a large range of organic waste.

To date, however, there are no or insufficient methods and devices available that can produce larvae of insects in an economically viable and efficient manner, in particular of two-winged insects, for example the black soldier fly.

Traditionally, larvae are grown in a breeding device, usually in the form of breeding cages, in which the relevant insects are placed and set to mate. Thereby material is provided in the breeding cages on which the pregnant female insects can deposit their eggs.

In order to remove the eggs from the breeding cages, keeping them until hatched and collect the neonate larvae in a separate recipient, several problems arise.

As a first step, the material with the eggs deposited on it should be removed from the breeding cages in order to harvest these eggs. This is accompanied by numerous problems and disadvantages:
1) the act of removing of this material itself is very labor-intensive;
2) this act disturbs the egg-laying and mating flies in the breeding cage;
3) flies escape from the breeding cage during this operation;
4) an incubation device or room must be provided to allow the eggs to hatch;
5) eggs that were not deposited on the "egg laying" material provided, must be separately searched for and harvested separately or will otherwise be lost.

After this, the eggs must be removed from the material on which the flies have deposited them. This process also involves many disadvantages:
1) also this process is very labor-intensive;
2) the total number of harvested eggs cannot possibly be precisely determined, because weighing and multiplying the number of harvested clusters with the average number of eggs per cluster yields a very rough estimate of the number of harvested eggs at best;
3) eggs are often damaged during manipulation, as well as in possible subsequent operations, so that the number of "still viable" harvested eggs is actually lower;
4) it is also unknown how many of the harvested eggs have been fertilized, as a result of which the actual number of "still hatchable" harvested eggs is actually lower;
5) finally, it is unknown how many of the fertilized harvested eggs are undamaged from these operations and are still in a sufficiently healthy condition so that they can effectively hatch.

As a result of all the issues listed above, it is impossible to determine, within a reasonable margin of error, how many live neonate larvae, i.e. larvae which preferably have been released that same day or at least during one of the past days, will be present in the recipient of the neonate larvae.

This large variation in the number of neonate larvae in the first phase of the process, causes that the next phase of the process, this is the rearing/growing of the larvae, is difficult to control and is unpredictable.

This rearing/growing takes place in bins, but the dimensions of these bins are fixed, meaning that when the number of larvae in the bin is not fixed, the space of these bins in this fattening/growing process is used sub-optimally. The Feed Conversion Rate in here is therefore far from optimal.

This inaccuracy on the number of eggs, and by extension the larvae in a recipient, also implies that the number of larvae must be estimated or calculated in a later phase so that the correct number of larvae can be put in a bin.

This gives rise to additional actions, and thus to additional working time and costs. It also results in a constant need to monitor the larvae breeding/growth process, to dose the right amount of feed to the number of detected larvae in the bin.

This in turn results in the need for a specialized feeding device and method that efficiently adjusts the volume of feed to the number of larvae present; this provides extra complex and consequently expensive devices.

The French patent application number FR 3 013 561, published on May 29, 2015, in the name of Pierre Furtos, discloses a device for the breeding of flying insects such as *Hermetia illucens*.

Likewise, the international PCT patent application number WO 2005/102368 A1, published on Nov. 3, 2005, in the name of Institut de Recherche pour le developpement, Paris, France, discloses a method for the biodegradation of protein- and/or fat-rich materials.

The problems and disadvantages of the state of the art as set forth supra, however, are not solved by the teachings of these two publications.

There is therefore a need for a method and by extension a device or apparatus in which the inherent disadvantages of the methods and devices known to date are avoided, and the larvae of these insects can be produced and counted in an efficient and economically justified manner.

More in particular there is a need for a method and a device or apparatus wherein the number of manual operations is limited to a minimum, the number of neonatal larvae produced can be collected efficiently in a recipient and the correct number of larvae collected in that recipient can be determined within a reasonable margin of error.

SUMMARY OF THE INVENTION

The goal of the present invention is to offer a solution to the aforementioned and other disadvantages, more specifically to provide the appropriate solutions to the issues mentioned above.

The invention essentially consists of a method for the cultivation and collection of larvae, preferably neonate larvae, more preferably one-day larvae.

To this end, the method contains the following steps:
a) placing insects in a cage and providing the female insects with materials for depositing their eggs;
b) ushering the larvae, hatched from the deposited eggs, by means of a guiding device, placed under the cage, under the influence of gravity to a conveyor belt placed under the guiding device;
c) transporting the larvae by means of the conveyor belt to a recipient placed at the end of the conveyor belt;
d) counting the number of larvae on the conveyor belt before collection in the recipient;
e) collecting the larvae of the conveyor belt in the recipient until a predetermined number of larvae has been reached.

The invention also relates to a device or apparatus for growing and collecting larvae, preferably neonate larvae. This device contains the following means:
a) a cage for placing insects, provided with means for depositing eggs by the female insects;
b) a guiding means, placed under the cage, for guiding larvae, hatched from the collected eggs, under the influence of gravity to a conveyor belt placed under the guiding means;
c) a conveyor belt for transporting or moving the larvae to a recipient located at the end of the conveyor belt;
d) a camera system for counting the number of larvae on the conveyor belt, before collection in the recipient;
e) a recipient for collecting the larvae of the conveyor belt until a predetermined number of larvae has been reached.

More particularly, the invention comprises the methods and the device or apparatus as described in the appended claims.

As further indicated, the method and the device according to the invention are valuable to use for the production of larvae, in particular of larvae of one of the following species:
Black Soldier Fly, Black Soldier Fly (*Hermetia illucens*);
Housefly, Common Housefly (*Musca domestica*);
Preferably the invention is applied to the larvae of the black soldier fly (*Hermetia illucens*) because these larvae are efficient processors of many types of organic waste streams.

BRIEF DESCRIPTION OF THE DRAWINGS

In order to better demonstrate the features of the invention, some preferred implementations of methods and devices are described below, as an example without any limiting character, with reference to the accompanying drawings or figures.

In these drawings the following is shown.

In FIG. 3, the following reference numerals indicate the following parts:
3.1 denotes the funnels support;
3.2 denotes the conveyor belt;
3.3 denotes the rotating cleaning brushes;
3.4 denotes the camera with lens;
3.5 denotes the conveyor motor;
3.6 denotes the lighting device;
3.7 denotes the electrical vibrator support.

In FIG. 4, details of the vibrating system are shown, whereby the following reference numerals indicate the following parts:
4.1 denotes the support for the electrical vibrator located on top of the conveyor;
4.2 denotes the vibrating blade hitting the belt;
4.3 denotes a fiberglass elastic junction (×4);
4.4 denotes the fixed support inside the conveyor;
4.5 denotes that the belt goes below the vibrating blade.

DESCRIPTION OF THE INVENTION

In the following description, we will further describe the various steps of the method according to the invention, as well as the various means in the device or apparatus according to the invention.
1. Cage (s) for Placing Insects.

Figure 1:
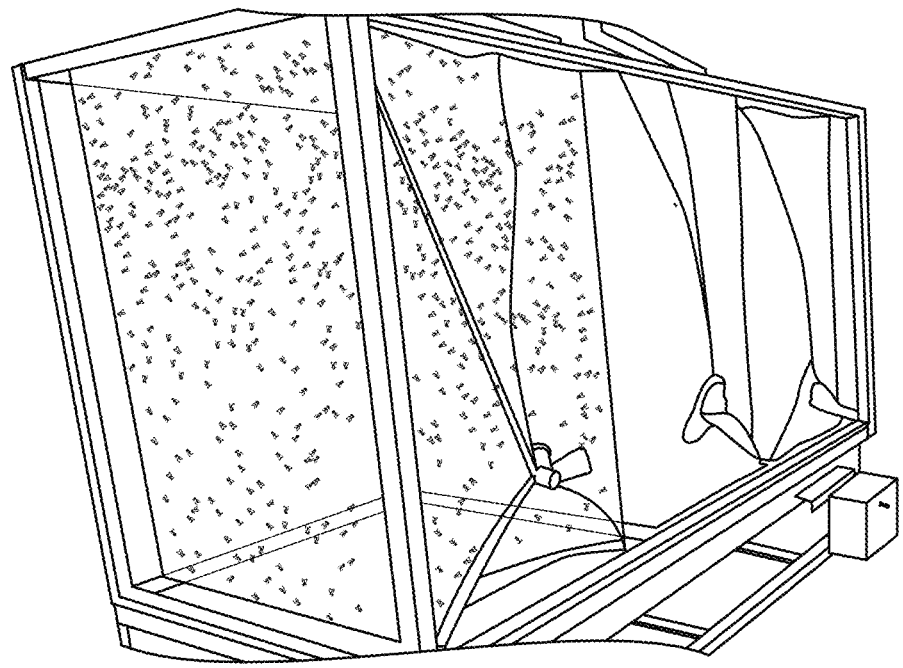
FIG. 1 shows a photograph of three cages for breeding the insects.

The first step according to the method of the invention, respectively the first means provided in the device according to the invention, relates to placing the insects themselves. This can take place according to the invention in a cage, an example of which is shown in FIG. 1.

In this cage, material for depositing eggs by the insects is provided. Several of these cages can be placed next to each other by means of one large frame. In FIG. 1, three cages are hung next to each other on one frame. The cages are regularly filled with insects, preferably with black soldier flies, preferably neonates. Such insects deposit large amounts of fertilized eggs on material that is provided for this purpose specifically in the cages. These recently hatched larvae end up in the cages themselves and fall through the bottom of the cage, thanks to gravity and are guided to a conveyor belt via a guiding device or guiding means, preferably funnel-shaped.

The design of the cage is kept as simple as possible, a rectangular cuboid with loops on all corners to stretch it out between 8 hooks attached to an external frame. Such a frame can carry several of these cages, as shown in FIG. 1, for example, for one frame comprising three cages.

When the cage design is kept simple, the number of corners, nooks and crannies is kept to a minimum. The female BSF will find every irregularity and consider it as an oviposition place. The following females that are searching for a place to deposit their eggs, will be attracted to these old clusters. When the eggs hatch, little to no neonate larvae will get lost, since sooner or later they will end up in the guiding devices under the breeding cages, and the conveyor belt, thanks to gravity. Most of the time the insects have a very passive behaviour and are perched on the sides of the cages. Using larger cages is to be avoided, since a lot of space is lost without actually being able to accommodate the amount of flies that is equivalent to the loss in space. It is mainly the walls, in particular the side walls, that have a useful purpose.

When working with thinner but longer cages, density (insects per surface area) can be easily increased, resulting in higher mating rate, resulting in higher production of eggs and thus neonate larvae.

On top of that, using multiple smaller cages, is preferred over a few large ones, since working in isolated units, isolates potential risks, ranging from teared netting and subsequent escaped flies to pathogens and predators.

In order to introduce new insects in the cages, an opening in the form of a sleeve can be provided for example, shown at the bottom right of the cages in FIG. 1. By opening this sleeve new insects can be introduced into the cage. After this, the cage can easily be closed again by, for example, tying a knot in this sleeve. This is shown in FIG. 1.

The cages are preferably made completely out of gauze netting. The maze diameter should be smaller than 1 mm. The maze diameter on the bottom of the breeding cage must be at least 1 mm in size, so that the neonate larvae can fall through, without being held back too much. The fabric itself should be durable and strong, permit easy maintenance and be machine washable. A good balance of "sturdiness" is also important. 100% polyester netting can be used in the methods and devices of the invention.

On materials on which the insect will deposit their eggs; these can be made from cylinders with slits placed on the bottom of the breeding cage. Ideally in a material that absorbs the smell of the insects and the eggs, but can be reused several times, such as wood.

The female insects usually look for narrow small gaps in the vicinity of decaying waste to deposit their eggs. The narrow spaces provide protection from dehydration and the decaying waste is a food source for the neonate larvae as soon as they hatch from the eggs. With these two parameters, the inventors have made numerous tests to steer the flies and have all the eggs deposited in a certain material that is easy to remove from the cage and then harvest the eggs. Tests were carried out with different shapes, materials and positioning of these structures, which were then also evaluated for user friendliness when the eggs had to be removed. Testing was also carried out by smearing these structures with attractive smells. In addition, other locations in the cage, which were frequently used by the flies as a place for their eggs, were smeared with scents that repelled the flies (mint, lavender, citronella, . . . ).

Although these tests had varying success, none of them were able to achieve a satisfactory result. In order to solve the problem of "lost" eggs, the inventors have finally come to the present invention, in which not the eggs themselves, but the (preferably neonate) larvae are harvested; in this way not only the loss of eggs/larvae is optimally reduced, but also the labor intensity of the method is considerably reduced.

By not harvesting the (fertilized) eggs, but the larvae, preferably the neonate larvae, and preferably the one-day larvae, it is no longer so important where the insects deposit their eggs in the cage. As long as this deposition takes place above the guiding device or means, they will sooner or later fall into the underlying guiding device at the time when the larvae hatch and so be guided to the conveyor belt.

2. Guiding Device

The next step according to the method of the invention, respectively the following device or apparatus provided according to the invention, concerns the guiding device or means for the hatched larvae. This device or means, placed at the bottom of the breeding cage, is used to guide the neonate larvae, hatched from the deposited eggs, under the influence of gravity to a conveyor belt placed at the bottom of the guiding device.

Figure 2:
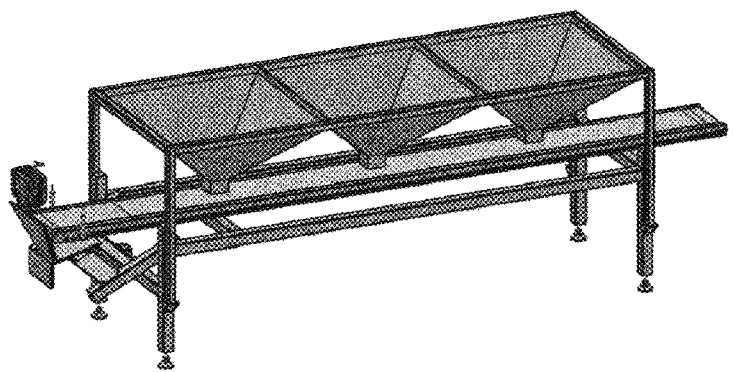
FIG. 2 schematically shows three guiding devices or means and the conveyor belt.

FIG. 2 shows a concrete embodiment of such a guiding device.

In this figure three such guide means are shown side by side, each suitable for placing at the bottom of a breeding cage.

These can for instance be funnel-shaped, in which the neonate larvae, result of the hatched fertilized eggs, fall under the influence of the gravity in the breeding cage in which the insects have deposited their eggs.

The preferably funnel-shaped guide means comprise smooth slopes, whereby the larvae slide off these sloping edges and thus end up on the conveyor belt at the bottom of these guiding device. In the manner described above, the larvae can be harvested from the breeding cages without any manual intervention, without there being a risk of damaging the eggs or neonate larvae.

On the moving conveyor belt, the larvae are then collected, counted as described below, and finally brought to a recipient, placed at the end of the conveyor belt. The side walls of the guiding means preferably lie at a slanting angle to the conveyor belt. This angle preferably lies between 30 and 70°, more preferably between 40 and 50°, even more preferably this angle is 45°. Below this angle, the larvae still slide sufficiently away from the walls of the guide means, and on the other hand this guiding means does not occupy too much height under the breeding cages.

In this way, the cages simply remain easily accessible to the operator of the device according to the invention. In a possible embodiment of the apparatus according to the invention, two rows of breeding cages are placed next to each other and, under each row of two breeding cages, one guiding device is placed, which catches the larvae of both cages and guides them to a centrally placed conveyor belt.

To this end, for example, cages with a square cross-section can be used with dimensions 60 by 60 cm. The guiding device then measures (60 cm×2)+10 cm extra handling space=130 cm in width, and 60 cm in the longitudinal direction of the guiding device.

As an alternative, it is also possible to work with one large funnel/trough under a single or double row of cages.

The material in which the guide means is designed is preferably as smooth as possible, in order to enable the recently hatched larvae to slide smoothly to the underside of the guide means and to receive the catch on the conveyor belt. The smoother the surface, the less likely the larvae stick to the sidewalls of the guide means or get enough grip to crawl back upwards.

According to practical tests carried out by the inventors, preferably polished material is preferably used, preferably polished stainless steel. For example, unpolished aluminum gives unsatisfactory results, not only because the larvae tend to stick to it, but also because it is much harder to clean.

3. Conveyor Belt

Figure 3:
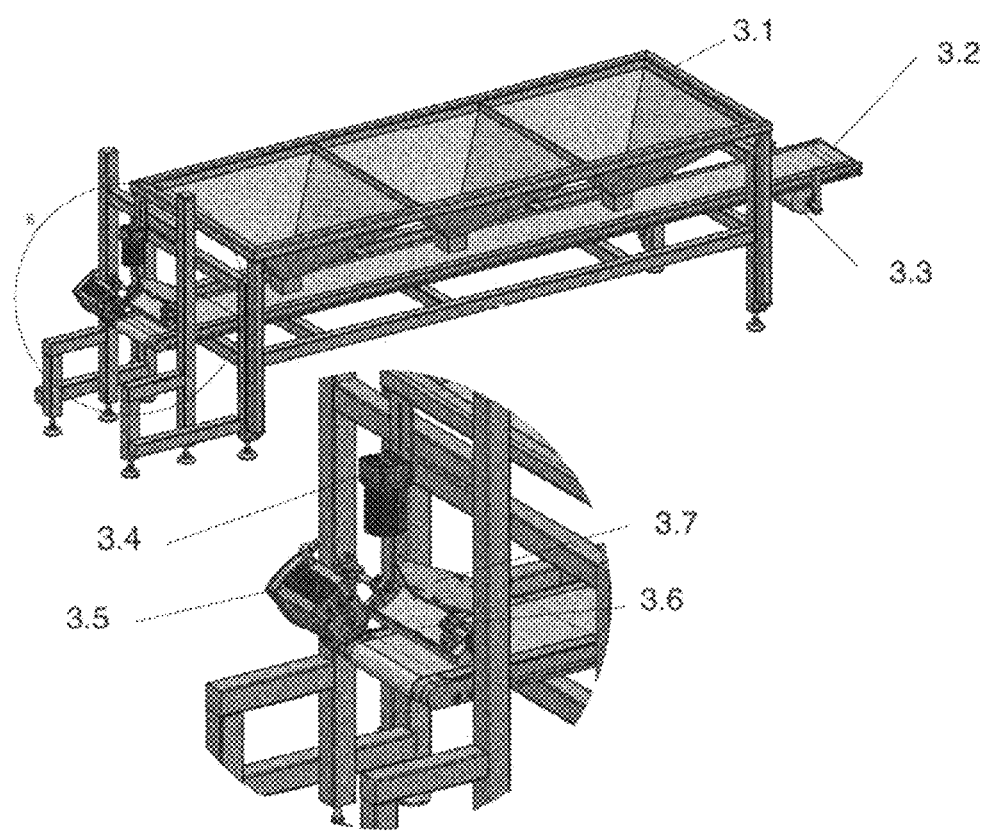
FIG. 3 again schematically shows three guiding devices and the conveyor belt, as well as in greater detail the end of the conveyor belt.

The next step according to the method of the invention, or the following means provided in the apparatus according to the invention, relates to the displacement of the larvae to a recipient placed at the end of the conveyor belt. For this purpose, a conveyor belt is provided at the bottom of the guiding device, as described above. Such a conveyor belt, shown for example in FIG. 2 or 3, comprises an endless belt which moves back and forth around at least two drive rollers, placed at the two ends of the belt. The conveyor belt then moves around these rollers, the top side in the opposite direction from the bottom of the belt. As soon as the larvae, usually one-day larvae, are hatched from the materials in the cages on which the insects have deposited their eggs, they fall down. Under the force of gravity, they are guided further downwards through the (preferably funnel-shaped) guiding device, towards (the top of the) conveyor belt, placed at the bottom of the guiding device. The conveyor belt is preferably driven at a constant speed via an electric motor. Near its end (the end of the conveyor belt seen in the direction of moving the top of the conveyor belt) a camera system has been placed for counting the number of larvae passing on the belt. At the end of the conveyor belt, especially at the turning point, the larvae of the belt fall into a recipient, positioned here for this purpose.

The inventors have found that the removal of the larvae from the surface of the conveyor belt in a number of cases is problematic.

First of all, the material of the conveyor belt must be selected in such a way that, on the one hand, its larvae fall off effortlessly at the turning point of the belt. To this end, the surface of the belt should be as smooth as possible. On the other hand, the smoother the surface of the conveyor belt, the more easily the larvae also drop off from the sides of the conveyor belt on the way from the point at the bottom of the guiding device on which they end up on the conveyor belt, to the end of the conveyor belt itself.

Increasing the speed of the belt reduces the chance that the larvae will fall off; however, a practical limitation has been imposed on this, since the camera system placed at the end of the conveyor belt must be able to accurately count the number of passing larvae on the belt. The processing speed of the images taken by the camera system of the larvae passing by on the conveyor belt is limited.

The width of the conveyor belt is also limited for an accurate recording by the camera system, larvae which must be exposed to lighting in an appropriate manner. The speed and material of the conveyor belt, as well as the color thereof, must therefore be carefully selected in order to tackle the challenges described above.

The rougher the material of the conveyor belt, the less easily the larvae fall off on the way, but it is more difficult to remove the larvae on the end of the belt.

The material of the conveyor belt must also be selected in function of an easy maintenance of the belt.

For this purpose, for example, a brush system can be provided, placed on the underside of the belt, which permanently cleans the belt by mechanical brushing action. Such cleaning is necessary because any dirt or unevenness on the belt by the camera system can be mistakenly regarded as a larva, and therefore incorrectly affects the correct number of larvae on the belt.

Finally, the material of the tire or belt should be chosen so that the maximum visual contrast between the tire/belt and the larvae present on the camera system is achieved. In this way, the processing and counting of the larvae by the camera system will be least susceptible to errors. In view of the latter, the use of a black-colored band is preferable.

A material that can be used for the conveyor belt of the apparatus and method according to the invention is, for example, the material marketed under the name "Habasit ENI-5EE PUR", Black conveyor belt. The width of the conveyor belt can be chosen within wide limits. The width preferably amounts to a maximum of 100 cm, and is preferably chosen between 5 and 25 cm, more preferably between 10 and 20 cm, even more preferably around 15 cm. With this width, the specifications of the cameras used and the number of cameras placed next to each other must be taken into account. The speed of the belt is preferably set between 0.5 and 20 m/min, more preferably between 1 and 8 m/min, for example around 4 m/min. This speed must be adjustable so that it can be adapted to the specific situation of the installation.

The conveyor belt can be driven, for example, by an electric motor with control unit from Nidec, Series DCK31 and type 404 991.

4. Vibration System on Conveyor Belt

One of the difficulties faced by the inventors is the removal of the larvae from the conveyor belt. The aim is that the larvae automatically fall off the belt at the turning point of the conveyor belt under the influence of gravity and are collected in the recipient placed for this purpose.

However, the larvae are somewhat sticky and therefore have a tendency to stick to the conveyor belt. This gives rise to numerous problems: first of all, such larvae are always counted by the camera system, leading to an incorrect count of the captured larvae.

Secondly they pollute the conveyor belt and are not or only partially removed by the mechanical brushing at the bottom of the conveyor belt.

Thirdly, such a soiled conveyor belt increases the risk that subsequent larvae also stick to the belt.

The inventors have tested numerous alternative methods and systems to solve this problem, in particular blowing a concentrated controlled air column over the conveyor belt, placing a scraping knife at the level of the barrier of the belt, or just below it.

The only method that yielded satisfactory results was to vibrate the conveyor belt at the level of the tipping point. The exertion of such a vibration on the conveyor belt ensured that virtually all larvae were unloaded from the belt under all circumstances and were collected in the recipient.

Figure 4:
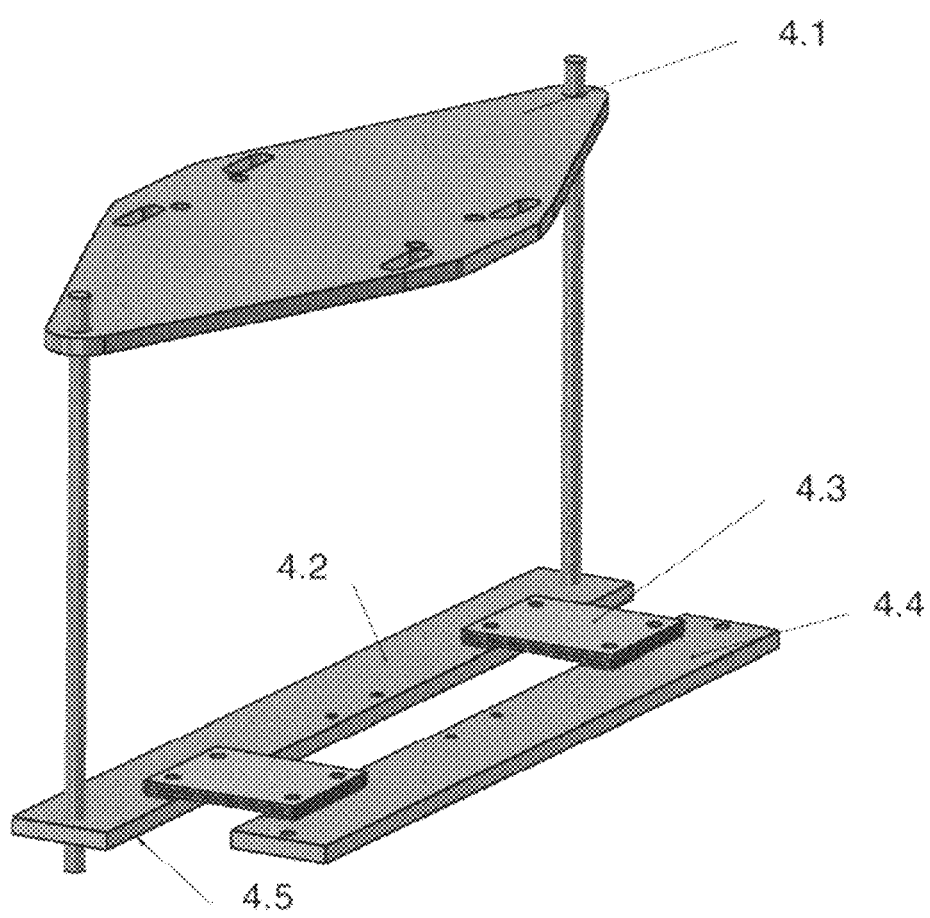
FIG. 4 shows the vibrating system and its support.

The vibrating unit used for this ensured that more than 99% of the larvae fell off the belt and ended up in the recipient. For this purpose, the vibrating unit should be placed at less than 25 cm, preferably at less than 20 cm, and most preferably at less than 15 cm from the reversal or inclination point of the belt. The vibrating unit which can be used for this purpose comprises, for example, the means shown in FIG. 4. In order to avoid interferences, the vibrating unit on the one hand and the camera on the other hand must be built up on separate supporting structures. Preferably use is made of an electric vibrating motor which transmits the vibrations on the conveyor belt via a transmission mechanism. The vibrations are preferably transferred to the conveyor belt shortly after it has rotated about its tipping point, and in a manner of speaking, starts the return path to its other end. The details of the vibrating system are shown in FIG. 4 and comprise the following means with their respective functions: a vibrating motor which is connected by means of a few rods, for example a pair, to an underlying blade vibrating against the inside of the returning conveyor belt, and so the neonate larvae shakes off the band.

According to a preferred embodiment of the invention, the vibrating unit consequently comprises a motor which transfers the vibrating function via a mechanism to the conveyor belt. A vibrating unit suitable for use in the method and apparatus according to the invention is the vibratory unit marketed under the brand name Italvibras II 3D tD A 22 IP65, ATEX 22.

5. Camera System

The next step according to the method of the invention, respectively the following means provided in the apparatus according to the invention relates to the camera system. This system serves to accurately count the number of larvae on the conveyor belt before collection in the collection tray.

This camera system comprises generally the following components:
a) a light source for illuminating the larvae on the conveyor belt;
b) a camera with lens for recording images of the larvae on the conveyor belt;
c) a program for counting the number of larvae detected on the conveyor belt via digital processing of the images recorded by the camera.

Figure 5:
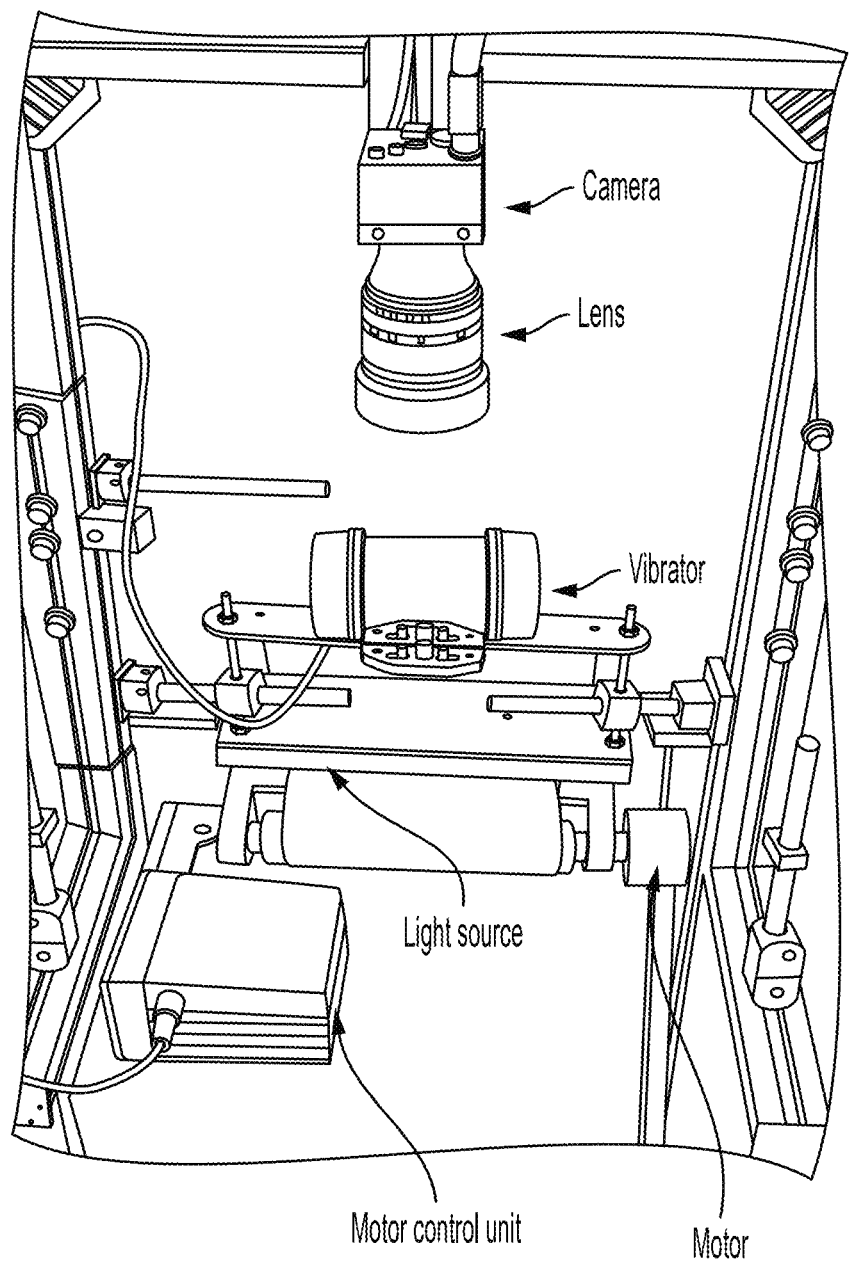
FIG. 5 shows a detailed photograph of the devices placed around the end of the conveyor belt.

In the FIG. 5 these different components are shown, as well as their respective position with respect to the conveyor belt of the apparatus according to the invention. The light source comprises a linearly designed source of light, which is placed across the full width of the conveyor belt, a short distance from the surface thereof. The head of the light source is turned slightly so that the light reflected by the larvae and the conveyor belt can be fully absorbed by the lens of the camera. The light source is placed just before the barrier of the conveyor belt, at the top of the conveyor belt. As a light source for use in the method and the device according to the invention, for example, the device can be marketed under the trade name Metalight Line Light Model: LL204.

The lens of the camera is focused on the surface of the conveyor belt. The camera with lens is also placed above the conveyor belt, also reasonably close to the barrier of the conveyor belt, in such a way that the light from the light source can be maximally absorbed by the lens. The camera records images of the larvae on the conveyor belt and passes them on to a digital image processing unit; this unit contains a program that shows the larvae, resp. clusters of larvae, and on this basis detects the total number of larvae on the captured images. These numbers are summed by the digital processing unit until a maximum preset by the user on this unit has been reached. In practice, this maximum is set to a range that depends on the size of the recipient. As soon as this number is reached, the processing unit gives a signal to the user of the device, for example in the form of a visual and/or acoustic alarm.

This is the signal for the user that the preset number of larvae in the collection bin or recipient has been reached. On receipt of this signal, the user or a machine removes the recipient filled with larvae, and places an empty tray at the height of the barrier of the conveyor belt.

The number of images made by the camera of the larvae on the conveyor belt depends on the speed of the belt. These images are then optically analyzed by the digital processing unit. To this end, this processing unit is provided with the necessary software. Examples of suitable software for use in the method and the apparatus according to the invention are the programs marketed under the brand name: Sapera Architect Software.

As camera for use in the method and the apparatus according to the invention, for example, the camera can be marketed under the brand name: Teledyne DALSA, model Linea M 4096-7 μm.

As a lens for use in the method and the apparatus according to the invention, for example, the lens marketed under the brand name Zeiss Planar T*1,4/50 ZF, can be used.

The digital processing unit processes the images of the larvae received from the camera in the next step sequence.

Figure 6:
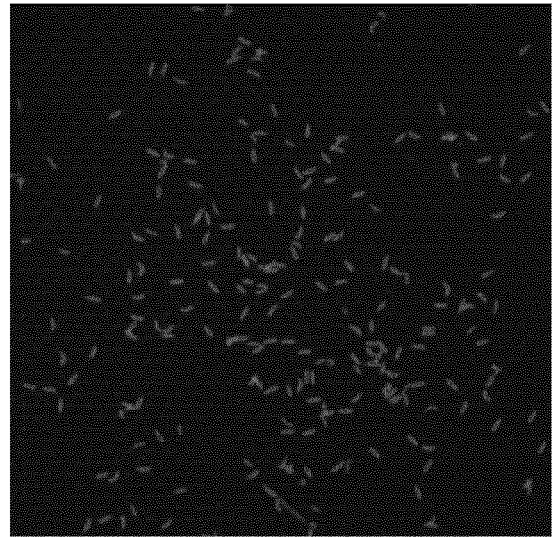
FIGS. 6 to 9 show images of the larvae on the conveyor belt, made with the camera system according to the invention.
Figure 7:
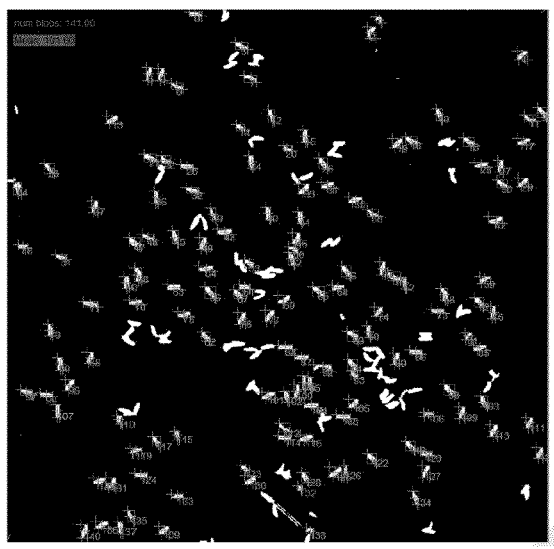

Initially, a binary image is extracted from the recorded images of the larvae. This is shown in FIGS. 6 and 7. The image processing algorithm recognizes individual larvae on the images on the one hand, and clusters or groups of (aggregated) larvae on the other. The individual larvae are 'recognized' by the image processing algorithm because their characteristic shape (a half-moon-like shape) and color (whitish) are stored as reference by the algorithm, and the digital data of the image is checked against this. This initially indicates the total number of individual larvae on the image.

The second phase is then to calculate the number of larvae coming from the clustered larvae on the image. The number of individual larvae in a cluster is given as input to the algorithm, the result of a preliminary test in which manually the number of individual larvae in different groups of larvae is determined by visual observation. The algorithm then calculates the surface area of each of the clusters of larvae on the intake, and calculates the number of larvae for each of the groups occurring on the basis of the average number of larvae per surface area.

This number is summed with the number of individual larvae, and the end result gives the total number of larvae in the shot. The inventors have examined the accuracy of the method described above by visual observation and manual counting of the number of larvae on different recordings; they have come to the astonishing conclusion that the method outlined above calculates the number of larvae with an accuracy of over 97 to 98%. In other words, the margin of error in the calculation of the number of larvae via the digital processing unit of the camera system is below 2 to 3%.

FIG. 6 shows an example of a recording by the camera system according to the invention; the resolution of the image is 780×768 pixels.

FIG. 7 shows the individual larvae on the image (bright white colored larvae).

Figure 8:
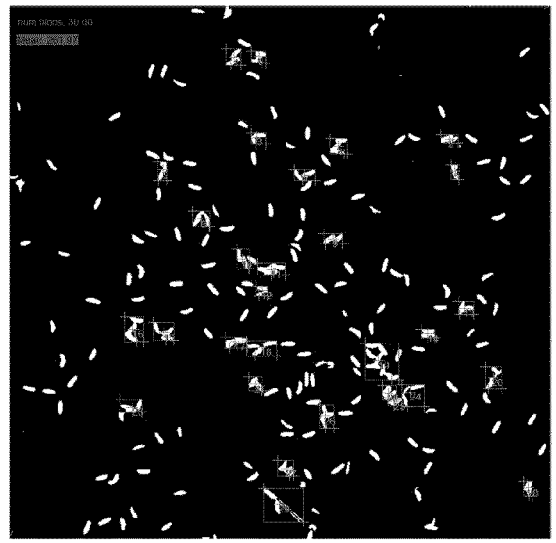

FIG. 8 shows the clustered larvae.

Figure 9:
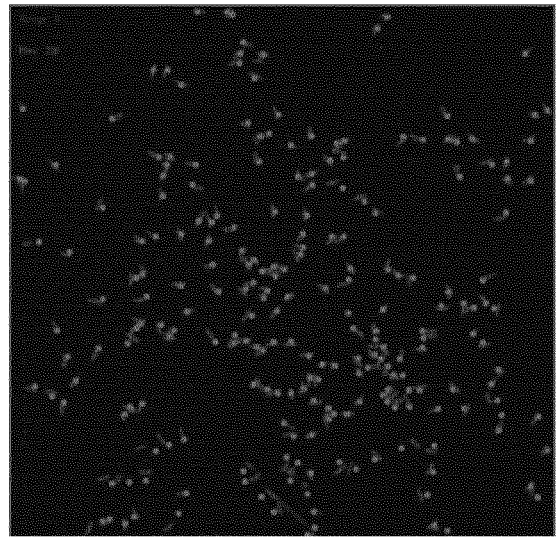

Finally, FIG. 9 shows both the individual and larvae clusters.

6. Recipient

The next step according to the method of the invention, respectively the next means provided in the apparatus according to the invention, concerns the recipient. This serves to collect the larvae from the conveyor belt and is filled until a predetermined number of larvae is reached. In a recipient with known dimensions, there is an optimal number of larvae that produce the most biomass in the shortest possible time span. 100,000 larvae per $m^2$ is a good standard. For a bin of 40 to 60 cm this means that 20 000 larvae fit. When it is possible to determine exactly how many neonate larvae end up in the tank, it is possible to determine exactly how much feed is to be administered in order to obtain an optimal growth curve. Even more important is that this can be determined in advance and that from day 1 everything in principle can go automatically, without having to make observations and adjustments to the frequency and quantity of feed.

Hence the importance of the correct determination of the number of larvae coming from the conveyor belt in the recipient of the apparatus according to the invention. At the moment the predetermined number of larvae is reached, the camera system gives a signal to the operator of the device, e.g. a visual or acoustic alarm signal. The user then removes the recipient filled with fresh larvae and places an empty recipient at the tipping point of the conveyor belt. The harvested larvae are then moved to a separate processing unit, in particular a rearing unit. In this unit, the (preferably neonate, more preferably one-day) fresh larvae are further fed until they can be further processed, as described in the above-cited Belgian patent application of the current applicant, BE 2017/0150.

The invention claimed is:

1. Method for breeding and collecting larvae, comprising:
   a) placing insects in a cage, provided with material for the female insects to deposit eggs;
   b) ushering larvae, hatched from the deposited eggs, by means of a guiding device, placed under the cage, under the influence of gravity to a conveyor belt placed under the guiding device;
   c) moving the larvae by means of the conveyor belt to a recipient placed at the end of the conveyor belt;
   d) counting the number of larvae on the conveyor belt before collection in the recipient; and
   e) collecting the larvae of the conveyor belt in the recipient until a predetermined number of larvae has been reached.

2. The method according to claim 1, wherein once the predetermined number of larvae has been reached, the recipient is removed and the method is repeated.

3. The method according to claim 1, wherein the insects belong to the species of the black soldier fly.

4. The method according to claim 1, wherein the removal of the larvae of the conveyor belt is facilitated by exerting a vibrating action on the end of the conveyor belt.

5. The method according to claim 1, wherein it is applied to one-day larvae.

6. The method according to claim 1, wherein the counting of the number of the larvae on the conveyor belt takes place by means of a camera system that:
   a) illuminates the larvae on the conveyor belt;
   b) captures images of the larvae on the conveyor belt;
   c) digitally processes the recorded images so that the number of larvae on the recorded images can be counted, and
   d) transmits a signal to the practitioner of the method as soon as a predetermined number of larvae has been reached.

7. The method according to claim 6, wherein the counting of the number of larvae on a recorded image comprises:
   a) recognition of individual larvae on an image and counting thereof;
   b) recognition of groups of larvae on an image, and calculation of the number of larvae per group by measuring the area of each group and multiplying the measured area of each group by the average number of larvae per unit area in a group;
   c) adding the numbers obtained under a) and b).

8. An apparatus for growing and collecting larvae, preferably neonate larvae, comprising:
   a) a cage for placing insects, provided with means for depositing eggs from the insects;
   b) a guiding device, placed under the cage, for guiding larvae, hatched from the deposited eggs, under the influence of gravity to a conveyor belt placed under the guiding device;
   c) a conveyor belt for moving the larvae to a recipient located at the end of the conveyor belt;
   d) a camera system for counting the number of larvae on the conveyor belt before collection in the recipient; and
   e) a recipient for collecting the larvae of the conveyor belt until a predetermined number of larvae has been reached.

9. The apparatus according to claim 8, wherein the guiding device comprises walls which guide the larvae from the edges of the breeding cage to the conveyor belt.

10. The apparatus according to claim 9, wherein the walls of the guiding device are made of polished material, preferably polished stainless steel.

11. The apparatus according to claim 9, wherein the walls of the guiding device are at an angle, measured with respect to the plane of the conveyor belt, from 30 to 70 degrees, preferably from 40 to 50 degrees.

12. The apparatus according to claim 8, wherein at the end of the conveyor belt the apparatus comprises a device that exerts a vibrating function on the end of the conveyor belt.

13. The apparatus according to claim 8, wherein the camera system comprises:
   a) a light source for illuminating the larvae on the conveyor belt;
   b) a camera with lens for recording images of the larvae on the conveyor belt; and
   c) a program for counting the number of larvae detected on the conveyor belt via digital processing of the images recorded by the camera.

14. The apparatus according to claim 8, wherein the conveyor belt is colored black.

15. The apparatus according to claim 8, wherein the larvae includes neonate larvae.

16. The method according to claim 1, wherein the larvae includes neonate larvae.

* * * * *